US008142799B2

(12) United States Patent
Sisco et al.

(10) Patent No.: US 8,142,799 B2
(45) Date of Patent: Mar. 27, 2012

(54) HIGH POTENCY CLINICAL ANTI-CRAVING TREATMENT AND METHOD OF USE

(76) Inventors: Tamea Rae Sisco, Centenniel, CO (US); Keith Kenneth Skinner, Honolulu, HI (US); Theodore R Keller, Centennial, CO (US)

( * ) Notice: Subject to any disclaimer, the term of this patent is extended or adjusted under 35 U.S.C. 154(b) by 1297 days.

(21) Appl. No.: 11/208,467

(22) Filed: Aug. 20, 2005

(65) Prior Publication Data

US 2005/0287226 A1 Dec. 29, 2005

Related U.S. Application Data

(63) Continuation-in-part of application No. 10/025,273, filed on Dec. 18, 2001, now abandoned.

(51) Int. Cl.
*A23L 1/302* (2006.01)
*A23L 1/304* (2006.01)
*A23L 1/305* (2006.01)

(52) U.S. Cl. ......... 424/400; 514/5.5; 514/474; 514/561; 424/630; 424/639; 424/641; 424/643; 424/655; 424/681; 424/702; 536/26.1; 607/900; 426/648

(58) Field of Classification Search .................. None
See application file for complete search history.

(56) References Cited

U.S. PATENT DOCUMENTS

| | | | |
|---|---|---|---|
| 3,697,287 A | 10/1972 | Winitz | |
| 4,005,190 A * | 1/1977 | Mader et al. | 424/679 |
| 4,282,863 A | 8/1981 | Beigler et al. | |
| 4,337,246 A | 6/1982 | Iwagiri et al. | |
| 4,528,197 A * | 7/1985 | Blackburn | 514/552 |
| 5,225,440 A * | 7/1993 | London et al. | 514/535 |
| 6,057,368 A | 5/2000 | Dewey et al. | |
| 6,132,724 A | 10/2000 | Blum | |
| 6,358,060 B2 * | 3/2002 | Pinney et al. | 424/435 |

(Continued)

FOREIGN PATENT DOCUMENTS

EP 558960 A1 * 9/1993

(Continued)

OTHER PUBLICATIONS

Page, Linda; "Stress & Energy: Reduce Your Stress & Boost Your Energy," 1999, Traditional Wisdom Inc.; pp. 58-65 (supplied as pp. 1-9).*

(Continued)

*Primary Examiner* — Cherie M Woodward
*Assistant Examiner* — Ivan Greene
(74) *Attorney, Agent, or Firm* — Fraser Clemens Martin & Miller LLC; J. Douglas Miller

(57) ABSTRACT

A practical high potency anti-craving medication is disclosed which comprises three components: an amino-acid component, a vitamin component, and a mineral component, wherein each component is selected for maximum efficacy in the body of an individual suffering from substance abuse disorder as opposed to the body of a healthy individual. Additionally, the active agents are received by means of a prolonged administration, preferably by means of an IV drip, thus assuring a period of time in which the active agents are present in desired concentrations, and more preferably a prolonged time during which they are simultaneously present in desired concentrations. The agents of each component are also selected so as to allow easy administration of the medication to patients in three vials of medication rather than as a large number of individual vials.

2 Claims, 9 Drawing Sheets

Figure 1:
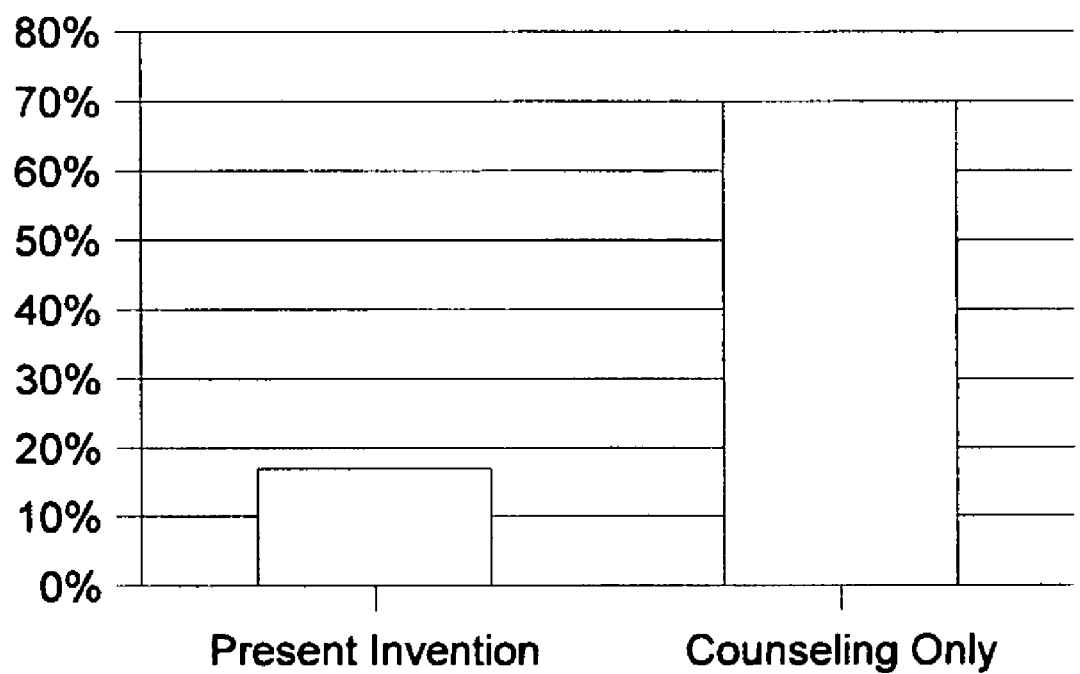

U.S. PATENT DOCUMENTS 6,955,873 B1 * 10/2005 Blum .................................. 435/6
2002/0172721 A1 * 11/2002 Boulos et al. ................. 424/646

FOREIGN PATENT DOCUMENTS

WO      WO 9848785 A2 * 11/1998
WO      WO 99/61038     * 12/1999
WO      WO 0126642 A2 * 4/2001

OTHER PUBLICATIONS

Derwent Abstract of EP 0558960 A1; Derwent Accession No. 1993-281577, (1993); Derwent Information Ltd; pp. 1-4.*

Newmeyer, John; Inaba, Barryl; Smith, David E.; Waldorf, Gary E.; Levine, Stephen A.; "Efficacy of Buffered Ascorbate Compound (BAC) in the Detoxification and Aftercare of Clients Involved in Opiate and Stimulant Abuse," From the Haight-Ashbury Free Medical Clinic, Jul. 1983; Jun. 1999 Focus on Allergy Research Group newsletter, pp. 1-5.*

Blum et al.; "Reduction of both drug hunger and withdrawal against advice rate of cocaine abusers in a 30-day inpatient treatment program by the neuronutrient Tropamine™", 1988, Current Therapeutic Research, vol. 43, No. 6, pp. 1204-1214.*

Blum et al.; "Enkephalinase Inhibition and Precursor Amino Acid Loading Improves Inpatient Treatment of Alcohol and Polydrug Abusers: Double-Blind Placebo-Controlled Study of the Nutritional Adjunct SAAVE™", 1989, Alcohol, vol. 5, pp. 481-493.*

Blum et al.; "Reward Deficiency Syndrome"; 1996; American Scientist, vol. 84, No. 2, p. 132(7-pgs.), (pp. 1-13 as supplied).*

The FDA Label for "Aminosyn II With Electrolytes"; retrieved from <http://dailymed.nlm.nih.gov/dailymed/about.cfm> on Jul. 1, 2011; pp. 1-8.*

Stadelman et al.; "Egg Science and Technology", 4th ed., 1995; The Haworth Press Inc.; pp. 177-183.*

* cited by examiner

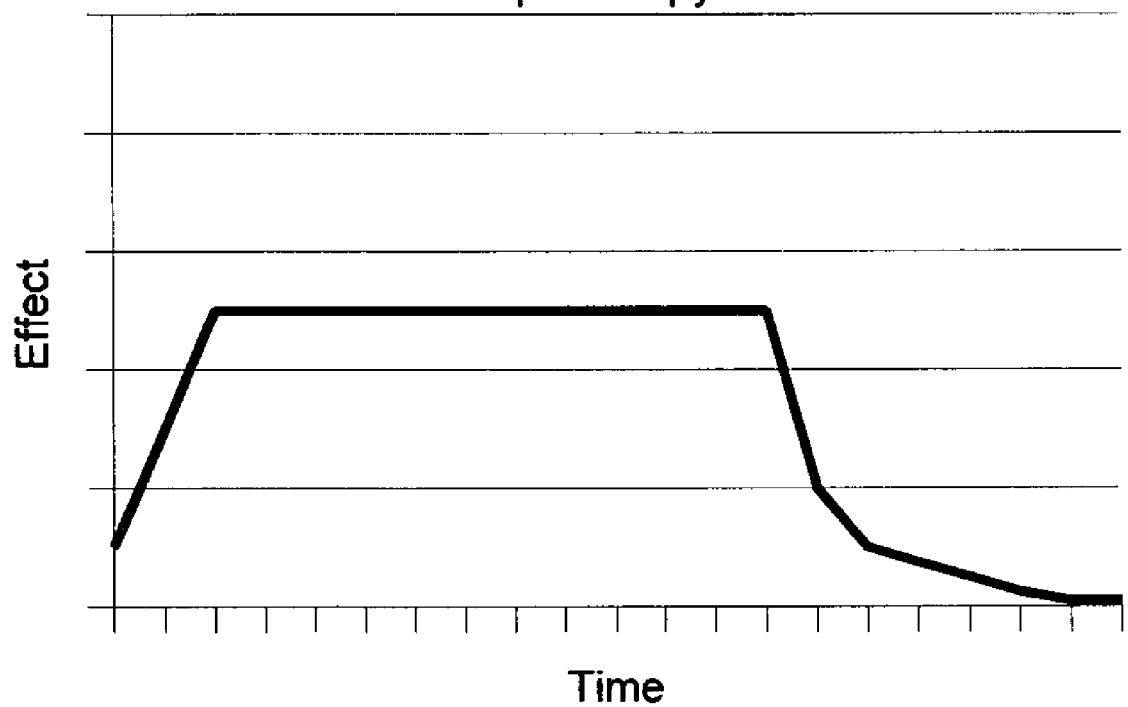

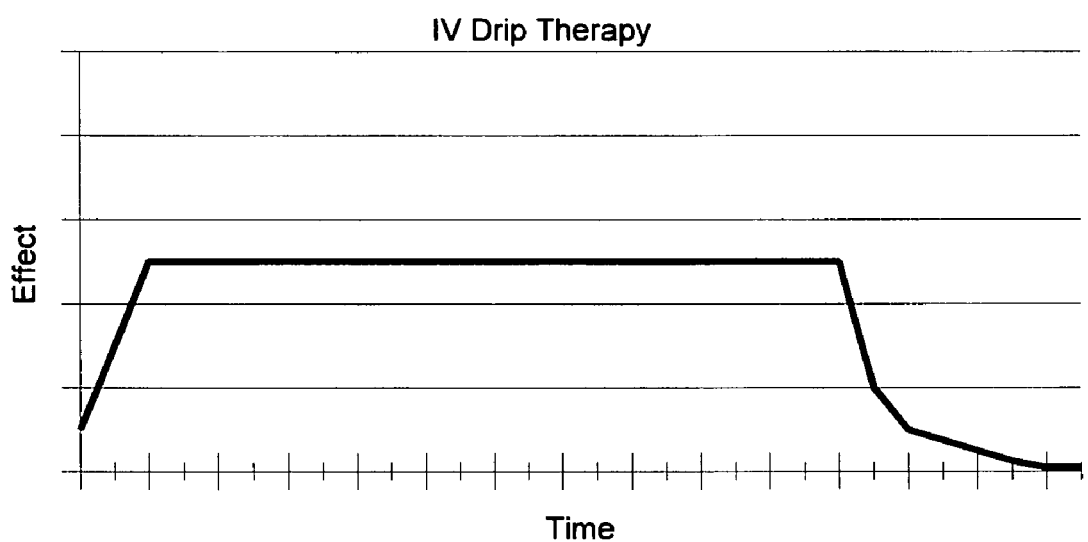

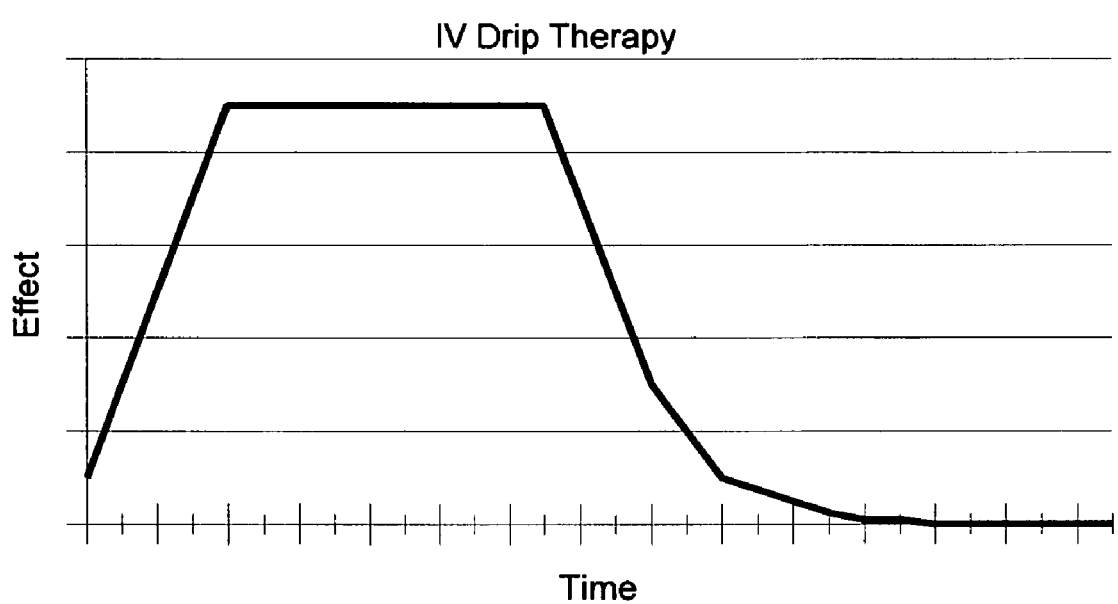
Fig. 3B - Increased Concentration

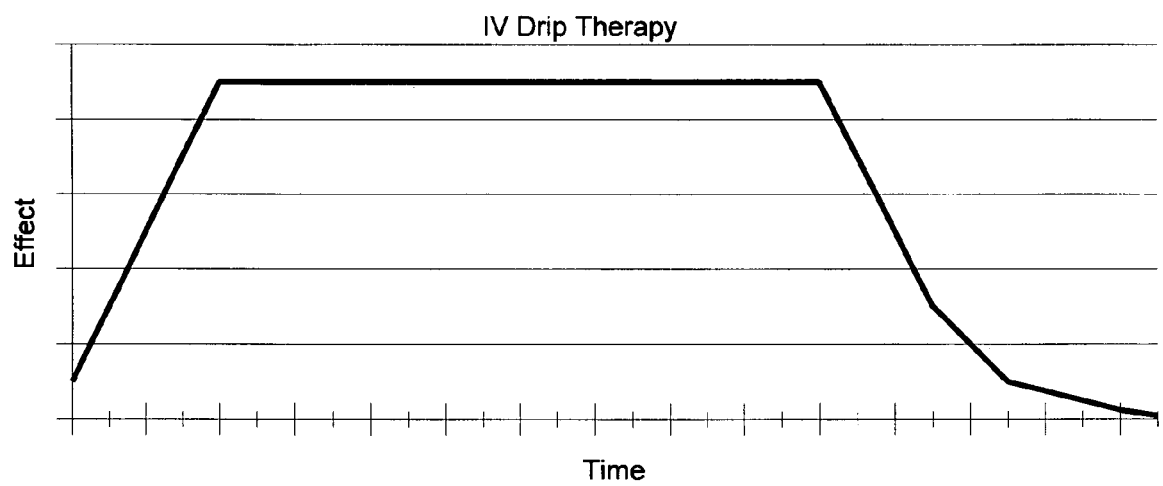
Fig. 3C - Increased Time and Concentration

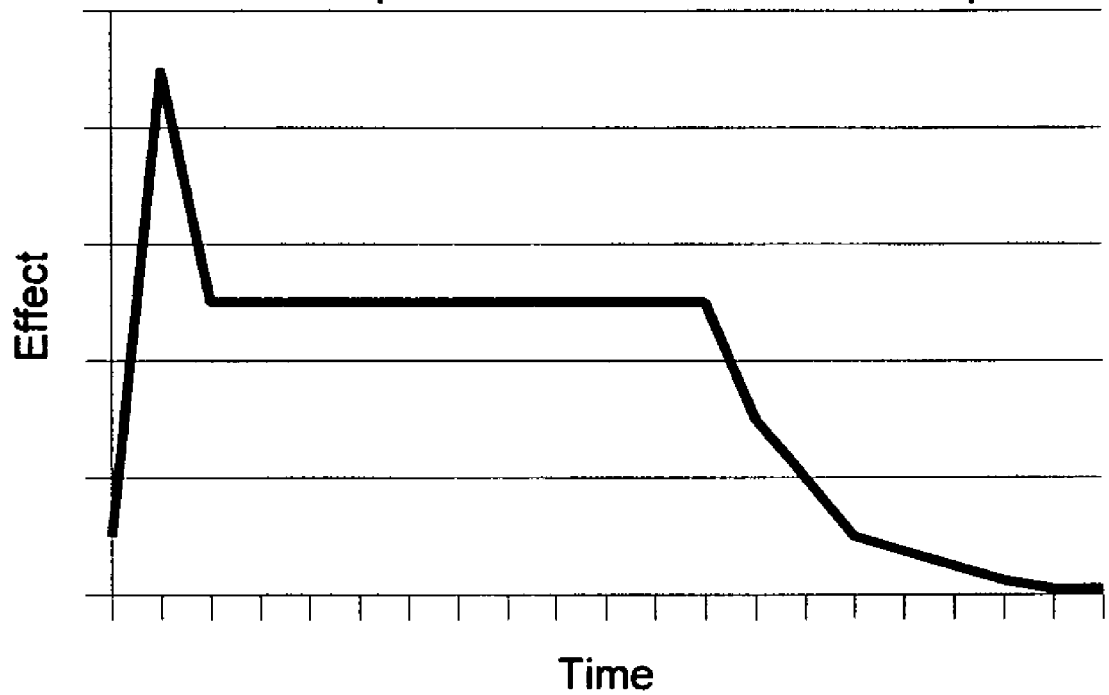

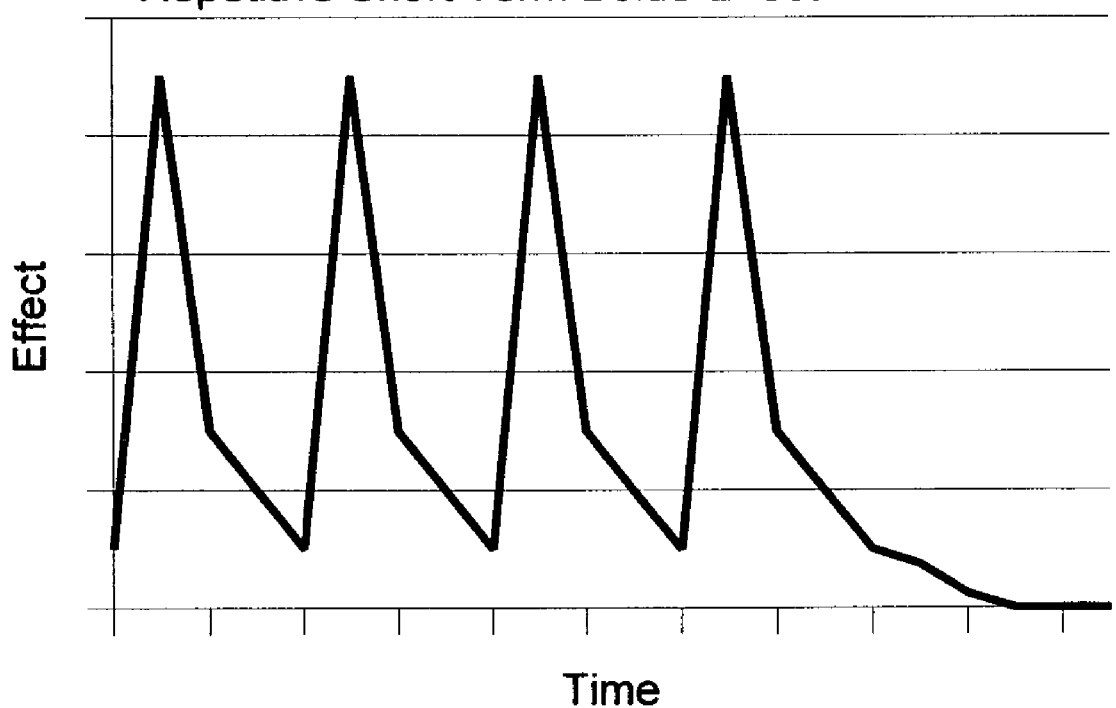

HIGH POTENCY CLINICAL ANTI-CRAVING TREATMENT AND METHOD OF USE

REFERENCE TO RELATED APPLICATIONS

This application is a continuation-in-part of U.S. patent application Ser. No. 10/025,273 having the same title and filed Dec. 18, 2001 now abandoned in the names of Dr. Tamea Rae Sisco, Dr. Keith Skinner, Dr. Albert Cileo, and Ted Keller, the disclosure of which is incorporated herein by this reference.

FIELD OF THE INVENTION

The invention relates to anti-craving treatments for patients suffering from substance abuse disorders (SAD). More particularly, the invention relates to an amino-acid anti-craving treatment offering high efficacy in patients having those health problems common among substance abuse sufferers.

STATEMENT REGARDING FEDERALLY FUNDED RESEARCH

This invention was not made under contract with any agency or body of the United States Federal Government.

BACKGROUND OF THE INVENTION

The societal consequences of the substance abuse disorders (SADs), cumulated over many millions of individuals, are well known. Every year, hundreds of thousands of lives are simply ended by substance abuse and related social problems, millions of lives are mined, and many millions of lives are adversely impacted directly and even more are impacted indirectly. The financial impact on society is almost as staggering: billions of productive days lost to SAD and secondary effects. This serves as one motivation for theoretical and laboratory medical research into the causes and cures for substance abuse disorders.

Horrendous as they are, such statistics pale in comparison to the results of substance abuse when the impact is measured on any given individual. Affected individuals usually suffer an almost total disruption of every facet of their previous lives: relationships destroyed, families disrupted or ripped apart, finances shattered, reputations mined, careers ended and the list goes on. For those on the "front lines" of addiction treatment, this serves as a very urgent motivation for practical and clinical medical research into the human conditions that lead to substance abuse or addiction. Medical research in the area is thus driven both from the top downwards and from the grass roots upwards.

Biological Bases of Addiction

In the last few decades, it has become increasingly clear on the theoretical side that addiction is in fact either largely or wholly a physiological disorder. Researchers have learned that in a few cases, a small number of genetic variations may be enough to provide an individual with a "predisposition" or "vulnerability" to addiction. It is also becoming clearer that a larger number of milder genetic variations may conspire together to create the same effect. Commonly abused substances themselves alter the function of the brain's normal pleasure response system, apparently as a result of the brain's adaptation to the substance. In fact, regardless of cause, the mere usage of certain chemicals (for example cocaine, alcohol, nicotine and morphine) is linked with changes in the brain's functioning and the associated craving for those substances. The result seems to be a grouping of very similar biochemical neuronal conditions which adversely impact the brain's pleasure responses. The term "Reward Deficiency Syndrome" (RDS) has been coined to describe these disorders. Estimates of the number of individuals that display RDS range as high as one third of the population. U.S. Pat. No. 6,132,724, issued on Oct. 17, 2000 to Blum and entitled "Allelic Polygene Diagnosis of Reward Deficiency Syndrome and Treatment" provides a great deal of background material on RDS and the probable genetic causes thereof.

The brain's neurotransmitter chemicals, receptor cells for those chemicals, and related systems regulating production and maintenance of the appropriate level of these neurotransmitters are at the center of this reward deficiency syndrome. For example, serotonin and dopamine have been implicated in this process: alterations in the metabolic cycle of these substances is part and parcel of substance abuse behavior and recovery therefrom. Dopamine levels may be reduced by substance abuse, and dopamine reception by the neurons may be reduced by substance abuse, thus forming one component of the craving for the substance. It is also possible that the individuals addicted to the substances in question had poor dopamine reception prior to the abuse behavior, and that the poor reception was part of the reason that the individual succumbed to the disease. More specifically it is known that dopamine release can be induced by application of precursor amino-acids, thus assisting in reduction of craving.

In addition to dopamine and serotonin, GABA and the opioid peptides are also believed to play a complex role in the reward process. For example, GABA may regulate dopamine release. Studies in rats and mice having a susceptibility to the abuse alcohol show low levels of serotonin and dopamine and increased levels of GABA and opioid peptides. One example of a patent for a medication which acts on the dopamine levels in the brain is U.S. Pat. No. 6,057,368, issued to Dewey et al on May 2, 2000 for "Treatment of Addiction and Addiction-Related Behavior." The medication taught by the '368 patent uses gamma vinyl GABA as an agent, and is not untypical of modern developments in treatment.

Treatment Regimes

In the past, addiction was treated as a moral or personal flaw, not a physiological condition. Thus treatment often was nonexistent. As the need for therapy became clear, early treatment regimes were instituted. Treatment often consisted of psychological support for the patient, or occasionally, not even that: in some nations, treatment consisted of forcing the individual to undergo "cold turkey" withdrawal in a prison cell. While psychological support for the patient is a necessary part of any treatment regime, methods based only on such support or in a worst case scenario on simultaneous deprivation of both substance and support were only partially successful.

There have been actual attempts to treat the underlying physical symptoms of the problem. Two methods involved in these early attempts to treat the physiology of RDS were the application of agonists and the application of antagonists.

Agonists are substances which themselves are received or otherwise stimulate reception of a neurotransmitter in the neurons, resulting in a "substitution" of one substance, the abused substance, with another: its agonist. The theory is that the craving will be satiated without recourse to the abused substance. Methadone is an example of a heroin agonist. While some positive results were achieved, it is uncertain if methadone treatment actually offered a higher rate of success than psychological support. Numerous "nicotine patches" are offered as a type of substitution therapy for nicotine addiction: while the agonist was in fact the abused substance nicotine, many other dangerous chemicals found in cigarettes, cigars and chewing tobacco are eliminated. In addition, the patient can control the dosage self administered, offering the opportunity to gradually end the nicotine dependency. However, most agonist therapies to date have suffered from a common weakness: they attempt to satisfy craving by replacing the desired substance with some other desirable substance, rather than by offering the patient's body the ability to return the patient's neurochemistry to a healthy state. Obviously, reduction of the craving would be preferable to merely satisfying it. In addition, certain agonist can themselves become addicting, and the patient's tolerance can increase, resulting in the need for higher dosages of the medication, not lower.

Antagonists, on the other hand, actually reduce the potency of the abused substance, resulting in reduced reward for its administration. Naltrexone is an example of a substance which blocks the effects of heroin. In this case, the operative theory is that with reduced reward, the individual will eventually cease to abuse the substance. However, the craving itself is not reduced, merely left unsatisfied by administration of the abused substance. Unfortunately, the action of blocking the effects of the abused substance is rather similar to simply denying the patient the substance in the first place: the craving remains, unsatiated. Worse, the patient's level of well-being spends long periods of time in the "anhedonia" or "dysphoric" (unhappy) phase of the abuse cycle, possibly inflicting as much pain as a "cold turkey" incarceration would have, and demonstrating no overwhelming reduction in the rate of recidivism. Even worse, the internal blockade of the abused substance may simply lead the sufferer to attempt greater dosages of it, with potentially catastrophic results. U.S. Pat. No. 5,824,684 issued to Viner on Oct. 20, 1998, may be taken as an example of a medication including an antagonist agent.

There have also been attempts to combine the agonist and antagonist therapies: See U.S. Pat. No. 5,935,975, issued to Rose et al on Aug. 10, 1999, for "Agonist-Antagonist Combination to Reduce the Use of Nicotine and Other Drugs". In the method, the agonist (or even the substance abused) is administered to the patient. At the same time or shortly thereafter, the subject is administered the antagonist to the abused substance. In theory, the approach leaves a lesser number of receptors available to respond to the abused substance, while at the same time minimizing the negative effects of a pure antagonist therapy. (See col. 4. lines 38-42.)

Each of these two methods and even combined methods such as the '975 patent do not attempt to return the neurotransmission system to a normal state. While therapy using an agonist temporarily reduces craving, the reduction is simply due to the administration of the abused substance or another having the same psycho-physiological effects. In no case is the actual source of the craving itself—the brain's neurotransmitter imbalances—really lessened, nor is the brain's reward system moved towards a normal balance.

Thus, new and promising therapies have concentrated on a different approach: craving reduction.

Craving-Reduction Therapies

One example of an attempt to treat substance abuse behavior is U.S. Pat. No. 5,013,752, issued May 7, 1991, entitled "Prevention and Treatment of Alcoholism by the use of Dietary Chromium." While the claim that chromium deficiency is by itself a cause of alcoholism is debatable, the use of chromium has become well established since that time as an ingredient in anti-craving compounds.

Amino-acids have been known for some time as potential agents for dealing with various conditions. U.S. Pat. No. 4,357,343 issued to Madsen, et al on Nov. 2, 1982, entitled "Nutritional Composition for Management of Renal Failure" is a typical example. A recent development in addiction therapy is the use of craving-reduction medications based upon amino-acid precursors of neurotransmitters such as serotonin and dopamine. In this approach, the patient is administered with an oral medication containing substances selected for their ability to promote healthy neurotransmitter function. Certain amino-acids are known to be precursors of the neurotransmitters. For example, the amino-acid 5-hydroxytryptophan is believed to be a precursor of serotonin while the neurotransmitter L-phenylalanine is believed to be a precursor of dopamine. Other amino-acids also function as metabolic precursors of the desired neurotransmitters.

Unfortunately the complexity of the human brain can substantially reduce the efficacy of merely providing a patient with a precursor amino-acid. The reward/pleasure system is not dependent upon any one single biochemical reaction, nor even upon a small number or class of biochemicals, nor does it occur in any one region of the brain. The interactions between the different chemicals in the human anatomy mean that even a subtly different medicinal formulation may have surprising or unexpected results.

In greater detail: the reward/pleasure response in the brain is a complex process in which stimulus in one part of the brain controls stimulus in others, which may in turn lead to stimulation of yet another part of the brain. Each of the steps of release, reception or uptake of neurotransmitters takes place at simultaneously at different locations, and for different substances, and different steps in the neurotransmission cycle may be under the influence of different neurotransmitters or other biochemicals: the release, reception or uptake of neurotransmitters is frequently under the control of other substances: amino-acids, vitamins and minerals. A short example is provided: a low level of a neurotransmitter in the brain can be partially or wholly offset by application of precursor amino-acids which help to build up the level. However, the level of the precursor amino-acids in the brain may be determined by their ability to cross the blood/brain barrier, which in turn may be governed by the amount of a given mineral in the blood stream. The rate of breakdown and maintenance of the same neurotransmitter in the brain may also be effected or even controlled at that point by the availability of some vitamin or mineral in the system acting upon the enzyme controlling the neurotransmitter. And a mineral which promotes the crossing of the blood/brain barrier by one amino-acid might act to reduce the crossing of the same barrier by other amino-acids. To provide details of this short example: L-tryptophan is a precursor which promotes neurotransmitter activities, while D-phenylalanine promotes neurotransmitter activity by inhibiting enzymatic cleavage. Administration of niacinamide, a form of the vitamin niacin, reduces the premature breakdown of L-tyrptophan in the blood stream because tryptophan is typically used in a 60 to 1 ratio to produce niacinamide. Niacinamide later appears to reduce the rate of serotonin breakdown in the brain by inhibiting the action of tyrptophan pyrrolase. The mineral calcium assists L-tryptophan to enter the brain, and then further assists conversion of tryptophan to serotonin, but drives other amino-acids into muscle tissue instead. L-tryptophan is desired for its ability to elevate serotonin levels, act as asleep agent, and reduce depression. When a patient is sleeping well and not depressed, the L-tryptophan may actually be removed from alternative embodiments of the present invention. Obviously while L-tryptophan is desirable, it is not desirable to encourage L-tryptophan's action at the expense of the other amino-acids used in the present invention. There are literally hundreds of such interactions taking place, creating a system too complex for present day modeling techniques to interpret.

Thus formulation of amino-acid based anti-craving medications is an unpredictable task, and anti-craving medications tend to involve a spectrum of ingredients designed to assist the combined efficacy or efficiency of the anti-craving effect. Examples of anti-craving compounds show the wide variation in formulations. For example, as referenced previously, U.S. Pat. No. 6,132,724, issued on Oct. 17, 2000 to Blum and entitled "ALLELIC Polygene Diagnosis of Reward Deficiency Syndrome and Treatment" provides a great deal of background material on RDS and the probable genetic causes thereof, and furthermore discloses and claims an oral anti-craving composition comprising a substance which inhibits the enzymatic destruction of a neuropeptidyl opiate, a neurotransmitter-precursor amino-acid, chromium, and either an herbal extract from *Rhodiola rosea* or huperzine. U.S. Pat. No. 4,761,429 ("Enkephalinase and Endorphinase Inhibitors as Anti-Craving Compositions", issued Aug. 2, 1988) and U.S. Pat. No. 5,189,064 ("Treatment of Cocaine Disorders", issued Feb. 23, 1993) both to the same inventor as the '724 patent, disclose craving reduction by means of administering amino-acids which "inhibit the destruction of neuropeptidyl opiates . . . in an amount sufficient to reduce the craving". The same inventor (Dr. Kenneth Blum, a leader in the field) has also stated that he has a pending patent application which was filed on Mar. 21, 2000, (application and number are unavailable to the present applicant) regarding short-term bolus administration of amino-acids and *Rhodiola* extract. Useful as these methods are, they nonetheless represent theoretical research towards the formulation of a compound of high efficacy. One result is that these compounds often do not take into account the special medical situations of typical substance abuse patients. For example, oral compounds are in practice administered with calcium, with consequent losses of efficiency due to the fact that calcium tends to drive several of the desired amino-acids from the blood stream into the muscles, rather than the across the blood/brain barrier. For another example, these three granted patents rely upon an oral administration of the medication. However, the typical substance abuse patient has severe damage to the stomach lining and intestinal tract caused by the ingestion of substances such as alcohol. Even individuals suffering the effects of intravenous substance abuse have stomach lining and intestinal damage. Thus, such oral formulations tend to pass through the digestive tract with relative alacrity and a low rate of absorption. As a result, the "amount sufficient to reduce the craving" is unnecessarily higher than it need be. But the stomach/intestinal lining damage is merely one practical barrier to efficient use of the medication by the body of the patient. In fact, the bodies of substance abuse patients present several barriers to the absorption, metabolization and usage of such compounds; these "substance-abuse derived" barriers will be discussed in the detailed description to follow. Another barrier to efficient usage of administered amino-acids, albeit a barrier present in all human beings rather than just those suffering from substance abuse disorder, is the blood/brain barrier. U.S. Pat. No. 4,650,789 and U.S. Pat. No. 4,897,380, respectively issued to Pollack and to Pollack, et al, on Mar. 17, 1987 and Jan. 20, 1990, for "Method and Composition for Increasing Production of Serotonin" and "Method and Composition for Relieving Dietary-Related Disorders" also propose amino-acid medications for neurotransmitter re-balancing. These two patents both teach the use of L-tryptophan as the amino-acid, along with ingredients designed to assist it across the blood/brain barrier. However, in order to assist L-tryptophan in crossing the blood/brain barrier, both patents suggest the use of fructose to drive other amino-acids in the patient's blood stream into the muscles, thus increasing the relative concentration of L-tryptophan and speeding its passage to the brain. Obviously, this is counterproductive if the objective is to administer a group of amino-acids.

Another example of this problem is the administration of cyanocobalamin (vitamin B12). While cyanocobalamin is the form of vitamin B12 which is metabolized in oral administration, and thus the form known in the art in anti-craving compositions, it is also a form which must first pass through the metabolic machinery of the liver to become hydroxycobolamin, then be metabolized by the liver a second time in order to become the metabolically active form of the agent vitamin B12. This known process is disadvantageous for use by substance abuse patients, as will be explained below in the detailed description of the present invention.

All of these compositions contain weaknesses in terms of their practical efficiency of use by the body of a substance abuser. In some cases, important components are administered in a form which decreases their ability to be absorbed into the blood stream at all. Some of the same references offer important active agents in forms which are slow or difficult to metabolize in the body of an individual who has abused substances. Other references teach the use of agents such as fructose which assist the use of one amino-acid at the expense of all others. Finally, compounding of numerous amino-acids, vitamins and minerals into a formula suitable for IV administration, with the consequent advantages thereof, is quite difficult. Amino-acid medications via intravenous drip may require the administration of a dozen or more vials of medication. Combinations of numerous ingredients, however, are likely to precipitate or react in storage. This both teaches away from the creation of multiple agent medications and also makes it difficult to find suitable formulas for such agents.

A second issue which arises is that of form of administration. The efficacy of a given medication will be a function of the concentration in the body of the individual achieved by a given method of administration and the time for which that concentration is maintained. Known oral medications are inefficient in terms of the concentration achieved. Direct injection via short-term bolus therapy on the other hand will merely "spike" the desired active agents in the body of the patient without providing a substantial amount of time for the agents to take effect. The knowledge that the active anti-craving agents would quickly depart the metabolic system appears to have caused previous researchers in the field to tend to avoid water soluble forms of the active anti-craving agents.

Thus, a need remains for an anti-craving medication which is formulated and administered for high efficacy due to the combination of active agents, but which is also formulated for efficient usage by the body of an individual suffering from the typical conditions of a substance abuser.

SUMMARY OF THE PRESENT INVENTION

The present invention has as an object and does provide an anti-craving medication for administration to the bodies of individuals suffering from substance abuse. The medication comprises a first component of selected forms of selected amino-acids, a second component of selected forms of selected vitamins, and a third component of the selected forms of selected minerals. The selection of the amino-acids and their forms, the vitamins and their forms, and the minerals and their forms is made based upon their combined ability to reduce craving. However, they are further selected so as to allow efficient use of the medication by such bodies of individuals suffering from substance abuse disorder, which customarily suffer from a number of conditions less common in the population as a whole.

The present invention provides an anti-craving medication whose selection of active agents is made so as to allow efficient use of the medication by the bodies of individuals suffering from substance abuse by promoting: crossing of the blood/brain barrier by at least one of said agents, liver by-pass by at least one of said agents, and stomach/intestinal lining by-pass by at least one of said agents. Selection of the agents includes not only selection of differing biochemicals but also different forms of those biochemicals. Such selection may be made on the basis of form, source, isomer, and other such criteria.

The present invention further provides an anti-craving medication whose ingredients are selected so as to allow each of said first, second and third components to be a single vial of medication suitable for intravenous administration, whereby a total of only three vials must be administered to such patient suffering from substance abuse, thereby allowing efficient use of the medication by such bodies of individuals suffering from substance abuse.

The present invention further teaches a method of administering an anti-craving medication to the body of an individual suffering from substance abuse, the method comprising administering a saline solution to the patient via intravenous drip, and supplying such anti-craving medication in said intravenous drip.

The present invention in another aspect provides an anti-craving medication comprising L-glutathione.

Yet another objective and aspect of the present invention is an improved anti-craving medication having a plurality of active agents wherein the improvement consists of selecting agents based upon their ability to by-pass metabolic processes.

Yet another objective of the present invention is providing an anti-craving medication comprising at least one member selected from the group comprising: riboflavin-S-phosphate sodium, dexpanthenol, niacinamide, folic acid sodium salt, methylcobolamin, inositol, and beet-source ascorbic acid sodium salt.

It is yet a further aspect, advantage, embodiment and objective of the present invention to provide an anti-craving medication whose ingredients are selected for fast effect on the patient to whom it is administered.

It is yet a further aspect, advantage, embodiment and objective of the present invention to provide an anti-craving medication for administration to the body of an individual suffering from substance abuse, said medication comprising: i) a first component comprising of the following agents: selected forms of selected amino-acids, ii) a second component comprising of the following agents: selected forms of selected vitamins, and iii) a third component comprising of the following agents: selected forms of selected minerals, wherein the first component further comprises: approximately 3.75 grams of D-phenylalanine, approximately 3.75 grams of L-phenylalanine, approximately 0.025 grams of L-tyrosine, approximately 1.2 grams of L-tryptophan, approximately 7.5 grams of L-glutathione, and water to bring the total volume to 1000 milliliters, and wherein the second component further comprises: approximately 1 gram of folic acid, approximately 0.2 grams of methylcobolamin, approximately 250 grams of ascorbic acid from a beet source, approximately 2.5 grams of thiamine hydrochloride, approximately 0.2 grams of pyridoxal-5-phosphate monohydrate, approximately 0.2 grams of riboflavin-5-phosphate sodium, approximately 5.0 grams of niacinamide, approximately 10 grams of dexpan-thenol, approximately 5 grams of inositol, and water to bring the bulk volume to 1000 milliliters, and wherein third component further comprises: approximately 4 grams of magnesium chloride, approximately 6.4 grams of zinc sulfate, approximately 0.786 grams of cupric sulfate, approximately 0.308 grams of manganese sulfate, approximately 0.01026 grams of chromic chloride, approximately 0.0196 grams of sodium selenite, and water to bring the bulk volume to 1000 millimeters.

It is thus another aspect, advantage, objective and embodiment of the present invention to provide an anti-craving medication for administration to the body of an individual suffering from substance abuse, said medication comprising: i) a first component comprising of the following agents: selected forms of selected amino-acids, ii) a second component comprising of the following agents: selected forms of selected vitamins, and iii) a third component comprising of the following agents: selected forms of selected minerals,
  wherein the first component further comprises:
  approximately 7.50 grams of D-phenylalanine,
  approximately 7.50 grams of L-phenylalanine,
  approximately 0.05 grams of L-tyrosine,
  approximately 2.4 grams of L-tryptophan,
  approximately 15.0 grams of L-glutathione, and
  water to bring the total volume to 1000 milliliters, and
  wherein the second component further comprises:
  approximately 2.0 grams of folic acid,
  approximately 0.4 grams of methylcobolamin,
  approximately 500 grams of ascorbic acid from a beet source,
  approximately 5.0 grams of thiamine hydrochloride,
  approximately 0.4 grams of pyridoxal-5-phosphate monohydrate,
  approximately 0.4 grams of riboflavin-5-phosphate sodium,
  approximately 10.0 grams of niacinamide,
  approximately 20.0 grams of dexpanthenol,
  approximately 10.0 grams of inositol, and
  water to bring the bulk volume to 1000 milliliters, and
  wherein third component further comprises:
  approximately 8.0 grams of magnesium chloride,
  approximately 12.8 grams of zinc sulfate,
  approximately 1.572 grams of cupric sulfate,
  approximately 0.612 grams of manganese sulfate,
  approximately 0.02052 grams of chromic chloride,
  approximately 0.0392 grams of sodium selenite, and
  water to bring the bulk volume to 1000 millimeters.

It is thus yet another aspect, advantage, objective and embodiment of the present invention to provide a method of administering an anti-craving medication to the body of an individual suffering from substance abuse, said method comprising: administering a saline solution to the patient via a prolonged intravenous drip, and supplying such anti-craving medication in said intravenous drip.

It is thus yet another aspect, advantage, objective and embodiment of the present invention to provide a method of administering an anti-craving medication further comprising: initially supplying a short-term bolus of such anti-craving medication via direct injection.

It is thus yet another aspect, advantage, objective and embodiment of the present invention to provide a method of administering an anti-craving mediation wherein said mid-term intravenous drip further comprises: continuing said administration for a period of time greater than approximately three hours.

It is thus another aspect, advantage, objective and embodiment of the present invention to provide a method of administering an anti-craving mediation wherein said medication further comprises: i) a first component comprising of the following agents: selected forms of selected amino-acids, ii) a second component comprising of the following agents: selected forms of selected vitamins, and iii) a third component comprising of the following agents: selected forms of selected minerals.

It is thus yet another aspect, advantage, objective and embodiment of the present invention to provide a method of administering an anti-craving mediation wherein the medication further comprises:

approximately 7.50 grams of D-phenylalanine,
approximately 7.50 grams of L-phenylalanine,
approximately 0.05 grams of L-tyrosine,
approximately 2.4 grams of L-tryptophan,
approximately 15.0 grams of L-glutathione,
approximately 2.0 grams of folic acid,
approximately 0.4 grams of methylcobolamin,
approximately 500 grams of ascorbic acid from a beet source,
approximately 5.0 grams of thiamine hydrochloride,
approximately 0.4 grams of pyridoxal-5-phosphate monohydrate,
approximately 0.4 grams of riboflavin-5-phosphate sodium,
approximately 10.0 grams of niacinamide,
approximately 20.0 grams of dexpanthenol,
approximately 10.0 grams of inositol;
approximately 8.0 grams of magnesium chloride,
approximately 12.8 grams of zinc sulfate,
approximately 1.572 grams of cupric sulfate,
approximately 0.612 grams of manganese sulfate,
approximately 0.02052 grams of chromic chloride,
approximately 0.0392 grams of sodium selenite, and saline solution.

BRIEF DESCRIPTIONS OF THE DRAWINGS

FIG. 1 is a bar graph showing comparative recidivism rates of the present invention versus counseling only treatment regimes.

Figure 2:
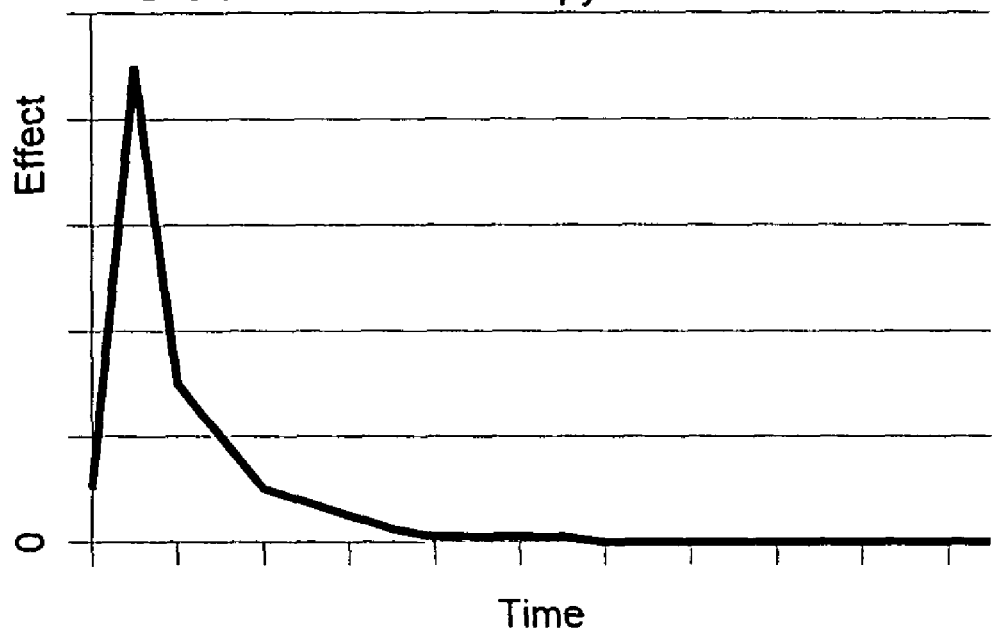

FIG. 2, PRIOR ART, is a graph of the effectiveness of short-term bolus therapy as measured by concentrations of active agents versus time.

FIG. 3. is a graph of the effectiveness of IV drip therapy as measured by concentrations of active agents versus time, for a first concentration and period of administration.

FIG. 3A. is a graph of the effectiveness of IV drip therapy as measured by concentrations of active agents versus time for a longer period of administration.

FIG. 3B. is a graph of the effectiveness of IV drip therapy as measured by concentrations of active agents versus time for a higher concentration.

FIG. 3C. is a graph of the effectiveness of IV drip therapy as measured by concentrations of active agents versus time for a higher concentration and longer period of administration.

FIG. 4 is a graph of the effectiveness of combined IN drip therapy and short term bolus therapy, as measured by concentrations of active agents versus time.

Figure 5:
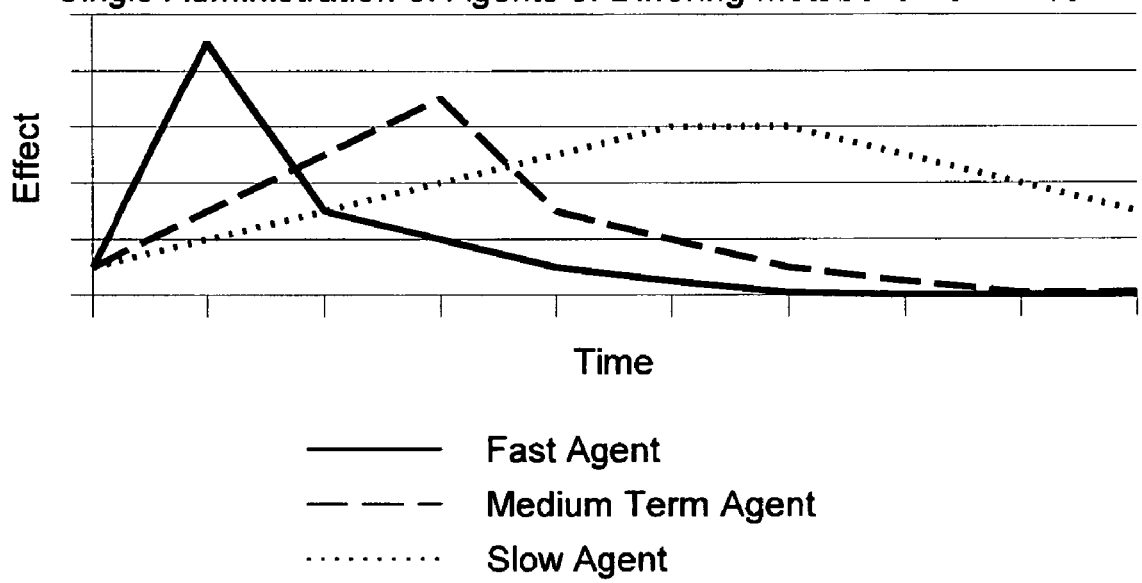

FIG. 5, PRIOR ART, is a graph of the effectiveness of three agents having differing metabolic half-lives when administered simultaneously, as measured by concentrations of the agents versus time.

FIG. 6 is not labeled prior art because applicant is presently unaware of any prior art to this effect. Thus FIG. 6 is a potential extension of the prior art from a single fast administration of a medication to repeated fast administrations of a medication.

DETAILED DESCRIPTION OF THE INVENTION

The invention provides an anti-craving medication whose active agents are selected to overcome the physical barriers to efficient use which exist in the bodies of individuals suffering from substance abuse; that is the agents are selected so as to allow efficient use of the medication by such a body of an individual suffering from substance abuse. The result is a medication offering high overall efficacy.

FIG. 1 is a bar graph showing comparative recidivism rates of the present invention versus counseling only treatment regimes. Recidivism rate, that is, the percentage of patients treated who return to substance abuse during or after treatment is a key measure of the overall efficacy of substance abuse medications. A lower recidivism rate is therefore much better than a higher recidivism rate. As stated earlier and shown on FIG. 1, counseling alone does not have a very high success rate: fully 70% of patients relapse at least once into substance abuse. While testing and accumulation of statistical data is not complete and the medication of the present invention has not yet been commercialized, the medication of the present invention is considerably superior to this counseling alone: only 17% of patients relapse into substance abuse. Longitudinal studies are on-going and double-blind studies versus other medications are under development.

The medication achieves this by selecting those forms of anti-craving agents which are most usable by a body suffering the disorders pandemic in substance abuse. Such disorders erect several physical barriers to efficient use of normal selections of agents for anti-craving compounds. To list several examples of such physical barriers: the stomach and intestinal linings of substance abusers are often damaged or simply dysfunctional, liver disease is quite prevalent among many types of substance abusers, substance abuse physically deprives the body of necessary nutrients (for example, by overusing the nutrients in the futile attempt to metabolize the abused substances at a rate sufficient to keep pace with the amounts the individual abuses) and psychologically deprives the abuser of the desire to follow proper nutritional guidelines; the poor nutrition endemic in this population then harms the abilities of the body to properly digest food and to utilize these nutrients and to assist the passage of the active agents across the blood/brain barrier, time factors work against the efficient usage of medications by those with substance abuse problems, and IV administration normally either requires a near instantaneous bolus therapy or else the usage of numerous vials of different medications. Workers serving the needs of patients addicted to substance abuse can see the effects of these barriers to efficient usage of medications—practical barriers which the highly intelligent researchers exploring the complexities of the neural pleasure/addiction processes may tend to deprecate or even overlook. At the same time, clinical workers tend to value ease of administration and long shelf life of medications and thus tend to favor oral medications or substances which can be injected by means of a short-term bolus under pressure.

"Metabolic by-pass" is crucial to the invention, this term includes by-pass of the liver ("liver by-pass"), stomach lining by-pass, intestinal lining by-pass, minimal use of the pancreatic juices, and the ability to cross the blood/brain barrier without reliance on metabolic resources. Agents are selected based upon their ability to by-pass metabolic processes. In particular, forms of the agents which can best by-pass metabolic processes are selected over forms which do not so easily do so. Forms of agents which require reduced metabolization, ideally, no metabolization, by the body of the patient are also called "active agents", "cellularly active" or "cellularly active agents" herein. The phrase "minimal metabolic processing" as used herein falls within the overall term "metabolic by-pass" and refers to a situation in which the disclosed and claimed metabolic by-pass is only partial, and some degree of metabolization is not avoided. Such minimal metabolic processing or minimized metabolic processing or reduced metabolic process is nonetheless described by the term "metabolic by-pass" as used herein.

Another important feature of the present invention is the application of medications over an extended period of time by means of IV drip rather than a single administration orally or by direct injection. Another important feature of the present invention is the careful compounding of the liquid components of the invention, each of which contains several active agents, so as to present as little challenge as possible to administration of the medication by IV drip.

Liver diseases most commonly associated with alcohol abuse strike the liver of users of many commonly abused substances. The liver filters out toxins, be they ethanol, cocaine metabolites, anabolic steroids, or any other substances. The results are cirrhosis and fibrosis, (gradual replacement of liver tissues with fat and connective matter), hepatitis and inflammation, portal hypertension, infection of the lobules, and other conditions. The net result is badly degraded liver function, resulting in difficulty metabolizing amino-acids and vitamins which the liver of a healthy individual would not have any difficulty breaking down into the proper form. Substance abusing individuals also generally suffer from poor nutrition and a low metabolic energy level which may not be up to the task of suddenly efficiently metabolizing a number of medicinal agents if administered orally, or up to the task of suddenly metabolizing agents administered intravenously if such agents are not provided in their final metabolically active or cellularly active form (or a form as close to that final form as possible), or even up to the task of metabolizing agents which are administered in a very short time frame (i.e. via short-term bolus). For example riboflavin (a B2 vitamin), an ingredient in known anti-craving medications, is normally absorbed by the intestinal lining and then metabolized by the liver into riboflavin-5-phosphate, the cellularly active form used by the body in neural functioning. Riboflavin-5-phosphate is a water soluble form which passes the blood/brain barrier. But very importantly, since riboflavin must be metabolized by the liver into riboflavin-S-phosphate before being usable, and since the typical substance abuser has liver damage, the efficacy of administered riboflavin is reduced. In addition, the substance abuser typically needs a prompt reduction in the physiological craving. Requiring metabolization of riboflavin by the liver not only reduces the impact of the riboflavin and requires metabolic energy, it also slows down the onset of the craving reduction. Even a parenteral administration of riboflavin via a direct injection of a short-term bolus to the patient does not alter the requirement for liver function to produce the form of riboflavin actually required. Since metabolization of riboflavin is a trivial task for a healthy liver, researchers have tended to overlook the entire issue. In addition, riboflavin-5-phosphate is not absorbed orally, a fact which militated against use of riboflavin-S-phosphate in known anti-craving medications. Selection of the riboflavin-5-phosphate form of riboflavin as taught by the present invention allows liver by-pass by the medication, that is, the medication is already in the form needed by the body of the patient, without liver interaction. Administration via IV drip allows stomach/intestinal lining by-pass, and using the form which passes the blood/brain barrier accomplishes the same function again. Selection of this form also provides greater effectiveness of the administered substance: to achieve an equivalent effect, 40 times as much riboflavin as riboflavin-S-phosphate must be administered and the body must metabolically process it, mostly in the very organ, the liver, which is usually hardest hit by substance abuse. Finally, prolonged administration via IV drip, as opposed to a short-term administration, a single bolus or a single oral administration allows medical personnel the opportunity to maintain a controlled concentration of the substance in the patient's system for a period of time. Thus the overall metabolic by-pass may comprise several steps, one of which is avoiding the use of substances which must be metabolized in the liver, referred to as "liver by-pass" herein.

Niacin (vitamin B3), another agent commonly employed in anti-craving medications, also requires metabolization by the liver into the water soluble form which passes the blood/brain barrier and is converted more quickly into stronger forms used in the brain. The present invention's teaching is that the combination of agents for the medication should be selected so as to avoid being inefficiently used due to damage to the body (especially the liver, in the case of niacin) of substance abusing individuals. This teaching leads, as in the case of riboflavin, to the concept that liver involvement should be avoided, which in turn leads to the conclusion that the metabolite of the niacin which is actually reaches and is used in promotion of amino-acid levels in the brain, that is, niacinamide, should be given directly, thus avoiding reliance on the (possibly dysfunctional) liver, reducing the drain on the metabolic resources of the patient, reducing the time required for the active form of the agent to reach the blood supply and increasing the period of time during which both the niacinamide and the amino-acids whose travel to the brain it promotes are simultaneously available in the blood supply. Inositol, another B3 vitamin, also is selected on this basis.

Glutamine is another example of an agent, in this case an amino-acid, for anti-craving formulas which under the teaching of the present invention should be replaced with L-glutathione. L-glutathione is useful as a single tripeptide in quenching/rescuing free radicals that interfere with normal cell metabolism. It prevents brain damage. It also increases levels of the neurotransmitter GABA; GABA promotes dopamine and other neurotransmitters. Thus, L-glutathione has properties which are very useful in anti-craving therapy. However, L-glutathione's use in anti-craving medications is believed to be unique and nonobvious for one of the same reasons which will be reiterated in relation to other amino-acid forms, vitamin forms and mineral forms used in the invention. Specifically, while L-glutathione is the cellularly active, "final form", or metabolite, which is actually used in neurochemistry of the brain, glutamine is the form which can absorbed after oral administration to the body of a healthy human being, and thus the form taught by the prior art. Giving an individual "off-the-shelf" glutathione would merely increase the metabolic load on the patient's body, which would be forced to reduce it to glutamine, at the time of ingestion, absorb it, then metabolize it internally into the desired L-glutathione. In order to provide the body with this beneficial agent and yet provide metabolic by-pass, the invention teaches that L-glutathione must be used instead of glutamine, that it must be injected by means of an IV drip, and furthermore, that the PH must be balanced. Normally, L-glutathione has a PH of between 2 and 3 and is not usable. At the time of compounding of the present invention, the L-personal digital assistant glutathione must have its PH increased in order to remove a sulfur molecule. While it is necessary to increase the PH above roughly 6.49 (a value which may be dependent upon technique used) in order to remove the sulfur molecule, at a PH above 7.2 the L-glutathione itself breaks down.

Metabolic by-pass of stomach lining, intestinal lining, liver and pancreas function also guides the selection of methylcobolamin, a water soluble and cellularly active metabolite of vitamin B12 which passes the blood/brain barrier. Normally, this form must be manufactured from inactive forms in the liver. Cyanocobalamin, the orally administered form, is first absorbed through the intestinal lining/stomach lining, and then converted by the liver to hydroxycobolamin. The hydroxycobolamin form is then converted, again by the liver, to the cellularly active methylcobolamin. Because Cyanocobalamin is the form absorbed by the stomach/intestinal linings of healthy individuals (and of course, absorbed at a reduced efficiency by substance abusing patients) it is the form taught in the references. The present invention teaches that metabolically by-passing the intestinal/stomach linings and the double load on the liver is desirable.

Diseases of the stomach lining and intestinal lining are also quite common in substance abusers. Alcohol releases free radicals on ingestion, in addition to the toxic effects of ethanol and other substances in alcohol. Even those who abuse substances self-administered by injection often experience such symptoms, due to the strong correlation between abuse of "schedule" substances and abuse of alcohol, which is known to injure the stomach/intestinal lining(s). In addition, other commonly abused substances, than alcohol also harm the stomach lining, by such mechanisms as gastritis (inflammation of the intestinal and stomach linings) and ulceration. Bleeding lesions, colitis and various cancers are further consequences of substance abuse suffered by the digestive tract and its linings. The extreme physiological stress often brought on by the impact on the individual's life caused by their substance abuse problem also leads to these forms of stomach and intestinal damage. Non-steroidal anti-inflammatory drugs (NSAIDs), commonly over-used by sufferers from most forms of substance abuse, also cause stomach lining injury. Renal and liver failure also lead to damage to the stomach lining, and as discussed in the previous paragraph, liver degradation is a "normal" symptom of the abuse of a wide range of substances beyond alcohol, even commonly injected substances or substances absorbed through the mucus membranes. Thus, the active agents mentioned earlier, and those mentioned later, may preferably skip the stage of absorption by the stomach linings and/or intestinal tract linings, which are respectively referred to as "stomach lining by-pass" and "intestinal lining by-pass" herein.

Broadly, the damage to stomach and intestinal linings appears to fall into two types: failure to secrete necessary digestive fluids (primarily a function of the stomach lining) and inability to absorb what is present in the digestive tract (primarily a function of the intestinal lining). Regardless of which mechanism is at play in the case of any particular medication or nutrient, the result is inefficient use of what passes through the digestive tract due to damage to the linings of the stomach and intestines. Pancreatitis is an acute inflammation of the pancreas, which prevents the pancreas from secreting digestive enzymes into the digestive tract. Pancreatitis is another disease common among certain types of substance abusers. The condition can be life threatening or so mild as to escape detection. Use of the enzymes secreted by the pancreas are another step in the normal metabolic process which substance abusers may be unable to do. Thus, by-pass of this step in the metabolic cycle is also taught by the present invention.

In practical terms, the ability of the typical substance abusing individual to absorb medications from the intestinal lining/stomach lining into the blood stream is reduced by other factors. The typical substance abuse patient has very poor nutrition and often very little solid S food at all in their digestive tract. Combined with an often chronically inflamed stomach/intestinal lining, the practical result is that the time available for ingestion of medications by the digestive system of a real-world patient is often much lower than the time available in the digestive system of a theoretical "healthy" substance abusing individual.

In addition, the malnutrition of such patients makes in incumbent that the medication "burn" as little as possible of the body's metabolic resources. Thus, the most efficient forms of the anti-craving substances are those which require the least metabolizing and offer the highest effect.

The time factor plays two further roles in guiding the selection of agents (amino-acids, vitamins, and minerals) for use in the medication. First, the agents chosen should be available to the patient's body at approximately the same time. For example, a synergistic effect of L-tryptophan, magnesium and riboflavin-S-phosphate is desired so it is counterproductive to allow one or more of the three agents arrive at a different time from the other agents. Selecting the forms necessary to achieve the correct time of metabolization, as taught by the present invention, assists in making sure that the agents are simultaneously present in the desired systems at the desired times. Providing administration over a period longer than a single bolus also acts to keep the desired mixture of biochemicals in simultaneous circulation. At the same time, it is desirable to provide some limit on the length of time and amount of effort required for administration.

The second time issue related to clinical needs is the speed with which the medication takes effect. The three components of the present invention allow for faster administration during emergencies in the clinical setting. In addition a "metabolic time lag", unpredictable even in an individual with a healthy metabolic system, can be avoided. It is also worth mentioning the background datum that intravenous administration is normally faster than oral administration. Speed of effect is of great importance in the clinical setting when dealing with patients who will sometimes be going through a fast paced physiological crisis, or who may allow medical staff only a short window of opportunity for providing treatment.

Once again, a delicate balancing of the time factors is required. The fastest possible administration (that is a single injection or a fast series of injections) is highly likely to result in different agents, which are supposed to be acting synergistically, to arrive in the blood stream and brain at different times. So while it is desirable to provide the fastest possible onset, it is also desirable to make sure that the speedy onset is not bought at the price of non-simultaneous arrival of the biochemicals. As an example, if a single injection is given containing both riboflavin and L-tryptophan, the riboflavin must undergo metabolic action by the liver before it can assist the L-tyrptophan's action. But the L-tryptophan concentration in the blood and brain will start to go down almost instantly after injection. Obviously, the riboflavin should be directly usable, and the two should be administered over a sufficient period of time for maximum combined concentrations to exist.

FIG. 2, PRIOR ART, is a graph of the effectiveness of short-term bolus therapy as measured by concentrations of active agents versus time.

The effectiveness of an agent is a function of at least two factors: instantaneous effectiveness, which depends upon concentration, and the length of time for which that instantaneous effectiveness (concentration) is maintained. Thus, instantaneous effect tracks concentration, but overall effectiveness depends on an integration of instantaneous effect with respect to time. Viewed graphically, this is easy to measure: the area under the graph of concentration's instantaneous effectiveness, integrated across time is the overall effectiveness of the agent being examined.

Concentration may be taken a number of ways: concentration in the brain fluids, concentration in the blood stream (not as accurate but considerably easier to measure) or other concentrations, i.e. versus the body mass of the individual.

FIG. 2, depicts the effectiveness of a single fast administration of an agent to a patient. This fast administration may be by several methods but is described as being short term bolus injection to the circulatory system. In other words, a needle and syringe with medication is being inserted into a blood vessel and the plunger is pushed with sufficient pressure to force the medication through the cannula of the needle into the blood vessel against the internal pressure of the human circulatory system. Such administration typically requires only a few seconds, which is in all likelihood one reason the prior art teaches in this direction. The bolus of medication will thus arrive in the system over the course of mere seconds. In the event of oral administration, the effect is slower but the overall shape of the graph is not significantly changed.

FIG. 2 shows the result in terms of instantaneous effect of the medicinal agent: a fast "spike" of very high value, then a rapid and asymptotic decline to a value near zero. The shape of the decline is determined essentially by the half life of the agent in the human body, and the desire for longer half-lives may have led prior-art researchers to avoid forms of agents which were highly soluble.

The overall effectiveness of the medication, the area under the graph line, is actually fairly limited. There is an extremely short time of extremely high concentrations (presumably, as high as good medical practice allows) and then a short period of very low levels during the asymptotic decline.

FIG. 3. is a graph of the effectiveness of the present invention administered via IV drip therapy as measured by concentrations of active agents versus time. Instead of a single fast administration, an IV drip is used. The medication, a quantity of sterile water, is injected into the saline solution bag and enters the patient's system slowly, via the IV drip. The result is a modestly prolonged administration. The timing of such an administration can be adjusted by adjusting the pressure exerted on the fluid entering the patient. While roughly 40-50 millibar is sufficient to overcome blood pressure between heartbeats, by adjusting the height of the bag or employing well known pumps which meter the dosage received by the patient, any exact rate of administration may be achieved. FIG. 3 depicts a time of administration ranging from a matter of minutes to approximately two to three hours in order to provide a convenient administration to patients: longer periods of time, while more effective, would be less clinically practical for patients, who may not have sufficient time available to the task.

FIG. 3 shows that the area under the graph is greatly expanded by this technique. The initial "spike" is removed, which reduces the immediate effectiveness of the medication, however, the overall effectiveness (concentration times time) quickly achieves higher levels.

FIG. 3A shows the results of using a longer period of time for a drip. This period of administration may be from roughly three hours to roughly six hours, preferably four to five hours. The area under the graph is substantially increased relative to the embodiment of FIG. 3: while less convenient for clinical patients (who do have practical time issues) this method of extended administration time greatly increases the amount of time spent with the proper levels and combinations of vitamins, minerals and amino acids available for metabolic bypass and use by the body of the patient.

FIG. 3B shows the effectiveness of an increased concentration of the invention administered for a period of time equivalent to that of FIG. 3. The effect of the therapy is greatly increased for that period of time. In clinical trials, the applicant has determined that extended periods of administration are preferable and more effective. Thus, a greatly increased period of administration, not just moderately prolonged but actively prolonged for an extended period of time, is greatly desirable.

However, it is noted that certain extremely practical limits pertain to this approach. Firstly, as with a "bolus" type administration, the amount of the therapy which may be administered is limited by the necessity to avoid over dosage of the patient. Obviously, at some level, the various compounds of the invention cease to be beneficial.

More subtly, however, the substances of the invention have certain maximum useful rates of metabolization. Administration of an amount in excess of that which can be usefully metabolized merely represents an extra strain on the system of the individual being treated. Of course there is no point in administering amounts beyond that which the human body can metabolize and use. More importantly, as noted, the bodies of most substance abuse disorder patients have severe chronic inability to metabolize substances as efficiently as is nominal. The first result is of course the need for metabolic bypass, but in addition, it would be desirable to avoid administering amounts during courses of time which would preclude use and would instead require disposal of the excess.

Thus, the chart of FIG. 3B is shown as reaching a "metabolically useful maximum level" at which it levels out. Thereafter, the concentration may be maintained but there is little purpose to increase beyond that metabolically useful level.

FIG. 3C brings together all of this. In the presently preferred embodiment and best mode now contemplated, the maximum metabolically useful level is achieved. However, as with the embodiment of FIG. 3A, the increased concentration of the IV drip therapy is maintained for a more prolonged period of time. In practice, a period of four to five hours is doable for patients in the clinical setting, and also efficacious in providing to the patients the desirable metabolically useful combination for an extended period of time. By means of this embodiment, the patient's body is able to hit a high level of useful metabolic activity of the compounds which decrease craving, pain, and other symptoms of the addiction, and is able to maintain this desirable state for a prolonged period of time. Note that a four hour administration, repeated daily for a period of days or weeks, results in a patient having the desirable levels within their system for fully ⅙ of the complete daily cycle.

On the other hand, FIG. 4 is a graph of the effectiveness of combined IV drip therapy and short term bolus therapy, as measured by concentrations of active agents versus time. This alternative embodiment appears to allow both the initial "spike" and a later time of high effectiveness. However, in practice, the initial spike is believed to be undesirable. Such brief high concentrations may cause an overload of the metabolic system, reducing the actual effectiveness of the medication to whatever the patient's body can actually metabolize, or even leading the patient's body to perhaps attempt to rid itself of the medication as quickly as possible.

FIG. 5, PRIOR ART, is a graph of the effectiveness of three agents having differing metabolic half-lives when administered simultaneously, as measured by concentrations of the agents versus time.

While FIG. 2 and FIG. 3 simplified the actual anti-craving medication to a single active agent, FIG. 5 addresses the fact that such medications may well be several agents. In FIG. 5, a single fast administration (for example of one short term bolus, or oral administration) is shown, with the instantaneous effectiveness of three different agents shown.

As stated previously, the brain's neurotransmission system is quite complex, featuring large numbers of interrelationships of neurotransmitters, pro-neurotransmitters, amino-acids, minerals, vitamins, and metabolites of these, all acting simultaneously on various different areas of the brain. Thus, anti-craving medications may have several agents which attempt to achieve the necessary synergistic effects in the brain, that is, all agents should be present, at the right time and in the proper, cellularly active forms, for maximum effectiveness. The synergistic effects of having, for example, a pro-neurotransmitter, a mineral helpful for its passage of the blood/brain barrier, and a vitamin which regulates the enzymes which break down the desired neurotransmitter are well recognized. FIG. 5 shows the results of a single fast administration of agents NOT selected for metabolic by-pass based upon the special needs of substance abusing patients.

The "fast agent" may be taken to be an agent which is absorbed quickly, perhaps even in the stomach, or after short term bolus injection requires no metabolization. The "medium term agent" may be taken as an agent which is absorbed more slowly, or must be metabolized by the liver into the cellularly active form, or is slow to cross the blood/brain barrier, or is otherwise delayed in reaching the brain or bloodstream in the proper form for use thereby. The slow term agent may be an agent which is absorbed very slowly, or perhaps requires multiple steps of processing by the liver in order to achieve the cellularly active form, or otherwise is delayed more than the other two agents in reaching the brain or bloodstream in the proper form for use therein.

In FIG. 5, there is a clear reduction in the overlapping area under the three graph lines, representing the overall effectiveness of the required synergistic effects. At the time the fast agent is present in high concentrations, the other two agents are not yet heavily bioavailable, or may be bioavailable in the blood stream when they are needed in the brain. At the time of the medium term agent's maximum availability, there is a slowly increasing supply of the slow agent and a slowly dwindling supply of the fast agent, but this phase. Wit actually exists at all in practice, quickly gives way to the time frame when both the fast and medium term agents are in low concentration and the slow agent is readily available.

Thus, it is preferable to continuously supply the multiple required agents and thus guarantee their bioavailability in the blood stream and their availability in the brain.

As noted previously, FIG. 3A and FIG. 3C represent a prolonged period of administration, while other embodiments of the invention may have shorter periods of administration.

FIG. 6 is not labeled prior art because applicant is unaware of any prior art to this effect. Thus FIG. 6 is a potential extension of the prior art from a single fast administration of a medication to repeated fast administrations of a medication.

Note that for the sake of clarity, this chart shows only a single agent, unlike FIG. 5, despite the fact that administration of several agents is needed for maximum efficacy.

At each fast administration in FIG. 6, a new spike of high concentration is inflicted on the body of the patient. While the net effect is a theoretical improvement of the area under the chart (instantaneous effectiveness as function of instantaneous concentration, integrated over time), the presence of the spikes makes the likelihood of systemic overload more likely.

Since FIG. 6 is a simplification, the actual effect of multiple fast administrations of medicines containing multiple agents would be numerous spikes of different agents at different times. In this regard, it is worth noting that some prior art references disclose ten or twenty agents.

It should be noted that in alternative embodiments of the invention, the selected active agents are administered sequentially via IV drip and thus metabolic by-pass is still achieved. The IV drip administration is still used as part of the metabolic by-pass (i.e. by providing fast acting water-soluble forms which do not require absorption or liver action), but the effect described above of modestly prolonged simultaneous bioavailability is not utilized.

Another factor relating to selection of ingredients for anti-craving medications is the ease of the combined ingredients crossing the blood/brain barrier. The poor nutrition of substance abusers is believed to negatively impact the ability of active agents to cross the blood/brain barrier. While getting the active agents into the patient's blood stream ("bioavailability") quickly is itself a victory, it is equally important to choose a combination of agents which promote crossing of the blood/brain barrier. As alluded to earlier, some prior art medications contain fructose, glucose, calcium or other agents which actually have mixed results in assisting a broad spectrum biochemicals across the blood/brain barrier. Tryptophan, for example, has a lower affinity than other amino-acids for the protein which carries the amino-acids across the blood/brain barrier, and furthermore the poor nutrition of many substance abusers tends to result in a comparatively low concentration of tryptophan in the blood in any case. One known solution is to use calcium to drive the "competing" amino-acids out of the blood stream and in to the muscles, but this solution is only useful if tyrptophan is the only amino-acid of interest, In the present invention, tyrosine is also used, as it is a precursor to dopamine. The amount of tyrosine used is a factor of the maximum amount that can be administered without driving dopamine levels too high (or spiking them) and the limit placed on its use by its solubility. But use of calcium would undermine the use of tyrosine. Despite this contradiction, medications presently marketed do contain tyrptophan and other desirable amino-acids, yet also contain calcium. Thus the present invention teaches that in medications in which it is desirable to assist a number of amino-acids across the blood/brain barrier, it is preferable to omit calcium when selecting the ingredients of the medication. (On the other hand, the known action of chromium in unbinding tryptophan from albumin in the blood in order to increase the concentration of tryptophan available for transport across the blood/brain barrier makes it a more suitable selection, based upon the special nutritional deficiencies of substance abusing patients.)

In addition to the teaching of the present invention to avoid calcium (which is present in some lower concentration in the body in any case, even in a reduced concentration in the bodies of nutrition-deficient substance abusers) the present invention teaches that in anti-craving medications it is desirable to avoid not just the calcium itself but also forms of other agents which will release calcium. As another specific application of the present invention's teaching of the desirability of metabolic by-pass, pantothenic acid (i.e. D-calcium pantothenate) (broadly vitamin B5) should be avoided, as it will release calcium after administration. Accordingly, dexpanthenol is preferred under the teaching of the present invention. In addition, dexpanthenol is another water soluble form which easily passes the blood/brain barrier.

Obviously, crossing of such barriers as the blood/brain barrier is greatly facilitated by prolonging the period of administration. In clinical trials, the applicant has determined that extended periods of administration are preferable, and without wishing to be bound by any particular theory, it is believed that part of this is due to the fact that the combination ingredients, provided for an extended period of time provide a much greater opportunity for crossing the blood/brain barrier.

One final barrier to effective use of anti-craving medications is not premised upon the state of the patient's health but rather upon the practicality of administration of the medication. When providing multiple medical agents to patients, the greater the number of components to be administered, more difficulty in administration, the greater the resistance of the patient to the therapy, and the greater the commitment of health-care professional time necessary to begin the administration of them. This depends strongly on the method of administration. While a series of pills or syrups may be swallowed with relative speed and ease, each component of an IV drip treatment requires a span of time for the liquid solution to enter the veins through the IV drip needle, a factor which may have led previous researchers away from IV drip administration. When the number of solutions rises to a dozen or more, the result can be forcing the patient to endure an extended span of time hooked to an IV tube and bag just to receive a regular dose of medication.

Thus after realizing that metabolic by-pass and medium term therapeutic administration are beneficial, the next step is to attempt to formulate liquid medications having the maximum number of agents in the minimum number of liquid components. However, medical solutions containing multiple active ingredients must be carefully compounded to avoid engendering new problems. Different active ingredients may react with each other in unpredictable ways inside the vials of medication during storage. One problem is precipitation of the agents in the liquid medication, calcium, in addition to its other undesirable properties, is prone to precipitation. Another problem is direct reaction of the agents with each other. A sister problem with multiple agent formulas is chelation, that is, metallization of another product such as a carbon-based molecule. The resulting precipitated or combined or metal-organic chemical or salt usually no longer has the desired medicinal properties, may no longer be suitable (small enough) to pass through the cannula of the IV needle, and may even be dangerous to the patient if administered. Other reactions can occur. For these reasons, it is a further challenge in this area to select and group active agents which can be safely combined and conveniently stored with a minimized risk of chelation or other undesirable reactions.

Preservatives are not used in the preferred embodiments of the present invention, both to avoid allergic reactions and to avoid side effects on organs already abused by too many toxins.

When several agents are compounded together into one component of the medication, as in the present invention, the shelf-life of the product dwindles sharply. In addition, the amino-acid component of the present invention contains L-Glutathione at a PH value of roughly 7, and this undergoes PH breakdown in a few weeks. Other amino-acids breakdown as well. Light hastens this process markedly and temperature has a similar important impact on shelf-life. Thus visual inspection is required before use by medical personnel, in order to verify that the product remains safe for use. These disadvantages are overcome by the formula of the present invention to the extent that a reasonable shelf-life on the order of 30 days is attained. Stability is another factor which has guided prior art research away from anti-craving medications for IV drip administration featuring active agents in the forms most useful to the body of the typical substance abuse patient.

Glucose and fructose solutions are not feasible for use in administering via IV drip multiple amino-acid medicines. First, the sugars "spike" the levels of the neurotransmitters in the brain much like the abused substance (sugar is often considered to be an abused substance itself quite apart from the fact that alcohols are sugars), thus included sugars would function as "agonists", reducing the craving temporarily by briefly satisfying it rather than by returning the brain to normal functioning. Second, fructose and glucose act much like calcium does, driving amino-acids into the muscle tissues rather than across the blood/brain barrier, and furthermore this undesirable activity is promoted by the presence of chromium and niacin, which are important agents for other reasons. Thus a saline solution is preferred, which in turn means that osmolarity of the IV solution becomes an issue as a result of the desire for a minimal number of components, at one component per vial, necessary for the administration. The concentrated form of the solution made possible by careful selection of the active ingredients can raise osmolarity above acceptable levels (10% for peripheral intravenous administration). Thus, compensation is required by reducing using a reduced saline solution. In the preferred embodiment of the invention, the saline is one half of normal concentration. At a kcal dosage of 275 kcal/ml, the osmolarity is approximately 295 mOsm/l.

Peripheral administration is preferable to use of a central venous catheter. While a central venous catheter allows administration of a medication having a broader range of Osmolarity than that allowable under peripheral administration, in the clinical outpatient setting the peripheral administration is more suitable, and the present invention teaches the peripheral administration is preferable. Unfortunately, due to the fact that many substance abusers self-administer numerous injections, resulting in a potential difficulty in location of a suitable peripheral vein, it is entirely conceivable that in the clinical setting a central venous catheter may nonetheless be required. Osmolarity needs to be controlled with great care in preparation of the medical components as above readings of approximately 500 mOsm/l, a stroke risk is presented. Osmolarity of 210-300 mOsm/l is believed to be safe for central venous catheter administration, while an 275-295 mOsm/l is preferred in the present invention, based on the preference for peripheral administration.

A further important issue which arises form the improved selection process for the agents in anti-craving medications is the criteria for exclusion of potentially beneficial agents by reason of the negative effects on the efficacy of the overall medication. Calcium has already been mentioned as a mineral agent to be deprecated, sugars are also to be avoided under the teaching of the present invention. L-glutamine can cause flu-like symptoms, and the special non-substance-related needs of the patient must also be addressed.

Obviously the medication must be administered in a dose sufficient to reduce craving by an individual for the abused substance they crave, for purposes of this document, the phrase "reduce craving" is taken to mean any degree of craving reduction whatsoever.

In addition to the usual factors which impact any dosage calculation for any patient, dosage calculation of the present medication depends upon a number of factors which relate specifically to substance abusing patients. The patient's degree of longitudinal sobriety is of primary importance: a patient who is still presently abusing the addictive substance will receive medication on a daily basis while those patients who have avoided substance abuse for a period of time will be on a maintenance regimen and will receive medication at a intervals of greater than one day. The second factor to consider is that of withdrawal symptoms: when the patient is in withdrawal from substance abuse, the need for anti-craving medication is obviously much greater. A third factor to consider is the presence of co-morbid health conditions, the fourth issue goes along with this: is the patient in pain, suffering from cancer or preparing for scheduled surgery. At least one of the agents of the present invention will reactivate dormant tumors which patients may have if the dosage is not proper; thus it is important to question patients carefully on all of these factors. Fifth, blood profile is of vital concern. Does the patient show signs (or test positive) for Hepatitis A, B or C, HIV, or do they show elevated liver enzyme levels? Finally, the patients use or abuse of other medications and allergies, while a standard medical question, is especially relevant to the substance abusing patient who may be sick and therefore properly receiving other medications or may be self-administering substances of their own choice.

Based upon such factors, the timing of the dosages, the strength of the dosages and the concentrations may be adjusted. In addition, it is also possible to adjust the formula for differing needs of differing individuals; the example of tyrosine is explained herein.

The formula of the a first embodiment is as follows:

TABLE ONE

The first component comprises:

approximately 3.75 grams of D-phenylalanine,
approximately 3.75 grams of L-phenylalanine,
approximately 0.025 grams of L-tyrosine,
approximately 1.2 grams of L-tryptophan,
approximately 7.5 grams of L-glutathione, and
water to bring the total volume to 1000 milliliters.
The second component comprises:

approximately 1 gram of folic acid,
approximately 0.2 grams of methylcobolamin,
approximately 250 grams of ascorbic acid from a beet source,
approximately 2.5 grams of thiamine hydrochloride,
approximately 0.2 grams of pyridoxal-5-phosphate monohydrate,
approximately 0.2 grams of riboflavin-5-phosphate sodium,
approximately 5.0 grams of niacinamide,
approximately 10 grams of dexpanthenol,
approximately 5 grams of inositol, and
water to bring the bulk volume to 1000 milliliters.
The third component comprises:

approximately 4 grams of magnesium chloride,
approximately 6.4 grams of zinc sulfate,
approximately 0.786 grams of cupric sulfate,
approximately 0.308 grams of manganese sulfate,
approximately 0.01026 grams of chromic chloride,
approximately 0.0196 grams of sodium selenite, and
water to bring the bulk volume to 1000 milliliters.

As noted, the timing of the dosages, the strength of the dosages and the concentrations may be adjusted. In particular, as noted in reference to FIG. 3 through 3C, increases in dosages up to some limit of metabolic usability may be contemplated. Doubling of the above formulation still produces a formula within the limits of metabolic usefulness imposed by the body of a patient suffering from SAD. Thus, the formula for a second, presently preferred embodiment, is as follows:

TABLE TWO

The first component comprises:

approximately 7.50 grams of D-phenylalanine,
approximately 7.50 grams of L-phenylalanine,
approximately 0.05 grams of L-tyrosine,
approximately 2.4 grams of L-tryptophan,
approximately 15.0 grams of L-glutathione, and
water to bring the total volume to 1000 milliliters.
The second component comprises:

approximately 2 grams of folic acid,
approximately 0.4 grams of methylcobolamin,
approximately 500 grams of ascorbic acid from a beet source,
approximately 5.0 grams of thiamine hydrochloride,
approximately 0.4 grams of pyridoxal-5-phosphate monohydrate,
approximately 0.4 grams of riboflavin-5-phosphate sodium,
approximately 10.0 grams of niacinamide,
approximately 20.0 grams of dexpanthenol,
approximately 10.0 grams of inositol, and
water to bring the bulk volume to 1000 milliliters.
The third component comprises:

approximately 8 grams of magnesium chloride,
approximately 12.8 grams of zinc sulfate,
approximately 1.572 grams of cupric sulfate,
approximately 0.612 grams of manganese sulfate,
approximately 0.02052 grams of chromic chloride,
approximately 0.0392 grams of sodium selenite, and
water to bring the bulk volume to 1000 milliliters.

Of course, the original limitation remains in place: the ingredients selected must provide an effective anti-craving medication when they finally reach the brain. But the selection of the ingredients should be modified based on the teaching of the present invention. As one example, copper, pyridoxine and ascorbic acid should be present in the medication in order to facilitate the conversion of tryptophan to serotonin, while magnesium facilitates the bonding of the serotonin to the neural receptors—but it is the teaching of the present invention that cupric sulfate, pyridoxal-5-phosphate monohydrate, sodium salt ascorbic acid from a beet source, and magnesium chloride are the particular forms selected for maximum efficacy under the disadvantageous conditions in the metabolism of the typical anti-craving patient. Pyridoxal-5-phosphate monohydrate, for example, is many times as powerful (possibly hundreds of times as powerful) as the pyridoxal HCL used in prior art references: pyridoxal-5-phosphate, the cellularly active metabolite, could not be absorbed orally (it would be broken back down to the pyridoxal HCL for absorption, then metabolized internally, in the liver, into the desirable form) and thus the prior art taught away from this cellularly active agent of the present invention.

The selection of minerals and/or vitamins possessing sodium (for example in the form of sodium salts) allows administration of an amount sufficient to reduce the need of the patient's body to add sodium to such minerals and/or vitamins in order to metabolize them into usable forms. Reduce in this case, refers to any degree of reduction whatsoever, of the need to add sodium, up to and including complete elimination of the need.

Phenylalanine is known to reduce enzymatic destruction of neurotransniuifters—it is the further teaching of the present invention that D-phenylalanine and L-phenylalanine are preferable to the racemic D-L-phenylalanine previously used. The preference for non-racemic phenylalanine is based on the desire to achieve as high a dosage as possible in a clinically practical small number of components and as small a dosage as possible. Unfortunately, phenylalanine has limited solubility. The D and L isomers of phenylalanine have separate saturation points, that is, separate maximum amounts which may be dissolved in the liquid of the amino-acid component of the invention. Thus, by using these two forms, double the amount of agent may be achieved per unit amount of liquid. Racemic phenylalanine may exhibit unpredictable and undesirable properties, such as covalent bonding, at the same concentrations.

In general, it is important to understand that the phrase "selection of forms" of active agents can thus refer not only to forms having different chemical formulas and different chemical names but also to forms which are isomers of each other. However, the active agents taught by the present invention are selected for reasons primarily related to the goal of effective use by the substance abusing patient's body. The preference for beet source ascorbic acid (vitamin C) is based on the potential for allergic reactions of patients to the normal corn source ascorbic acid, this is also a factor in avoiding the use of preservatives in the medicine. The conversion to a sodium salt is preferable for the same reasons discussed in regard to folic acid: a water soluble form passing the blood/brain barrier, elimination of need for sodium addition in stomach, etc.

Thiamine HCL is also a water soluble B vitamin which passes the blood/brain barrier. While the forms of these active agents which the present invention teaches are water soluble and pass the blood/brain barrier, other additional forms of these agents exist and may be used, which equivalent forms are relatively water soluble and/or also pass the blood/brain barrier.

This is yet another reason for the pains taken in selection and compounding of the present invention: the bodies of substance abuse patients are more prone to side effects, allergic reactions, other negative responses to medications. Consistent selection of active agents which avoid such reactions makes the present invention both superior to and admittedly more difficult to develop, compound, store and use than prior art medications. However, the present invention provides a medication with the bodies of substance abuse patients can more practically use with high efficiency.

The present invention teaches that cupric sulfate is preferred, in addition to the reasons stated, for the fact that it is a "small" molecule which more easily passes the blood/brain barrier. The phrase selecting molecular forms of minerals having small size, as used herein, refers to the size of the molecules as compared to the size of molecular forms such as oxides. This is true of several of the minerals which are used in their sulfate forms. The sulfate forms are also water soluble, another factor in assisting IV drip administration and thus use by bodies suffering from metabolic dysfunction. The phrase mineral forms which are water soluble, as used herein, refers to the degree of water solubility as compared to the solubility of molecular forms such as oxides. The chelated (often oxide) forms of these minerals taught by the prior art for oral administration are not water soluble, do not pass the blood/brain barrier and must be metabolized in the body, unlike the forms reached by application of the present invention. Thus the present invention teaches selection of non-chelate forms of the active agents (including amino-acids and vitamins, not just minerals). Sodium selenite is also provided for its high degree of water solubility. By contrast, the known agents magnesium oxide, manganese AAC, and chromium dinicotinate glaciate are not water soluble. These prior art forms were used because they were easily absorbed orally, whereas the forms used in the present invention, if administered orally, would have had be broken down in the digestive tract into such chelate forms or metabolites thereof, absorbed, and then metabolized internally in the more desirable, cellularly active final forms directly provided by the present invention.

All of the minerals must be administered in the proper ratios: in the wrong ratios, they will promote accumulation or disturb the natural balance of the nutrients they are designed to promote. Excess amounts may even suppress enzymatic functions rather than promote them.

The best mode presently contemplated, and the most preferred embodiment, has three components. Amino-acids are compounded into one component as the active agents thereof, physically this is a first vial of liquid suitable for injection into a saline solution IV setup. A second component contains vitamins as active agents in a similar liquid carrier (sterile water) and the third component contains mineral active agents in a sterile water solution. In use, the patient's IV drip receives a dose of each component, and the IV drip supplies the agents of the three components to the patient at a steady rate.

The present invention and the best mode presently contemplated thereof have been revealed so as to allow one skilled in the art to practice the invention without undue experimentation. While numerous details have been set forth for illustrative purposes, it will be obvious to those skilled in the art that the invention is susceptible to many equivalents, substitutions, and alterations without departing from the essential spirit and scope of the invention. Nothing in the foregoing disclosure is to be taken to limit in any way the scope of the invention, which is to be construed only on the basis of the appended claims.

What is claimed is:

1. A method of administering an anti-craving medication to the body of an individual suffering from substance abuse, the method comprising:

administering an anti-craving medication in an intravenous drip, wherein the anti-craving medication comprises:
7.50 grams of D-phenylalanine,
7.50 grams of L-phenylalanine,
0.05 grams of L-tyrosine,
2.4 grams of L-tryptophan,
15.0 grams of L-glutathione,
2.0 grams of folic acid,
0.4 grams of methylcobalamin,
500 grams of ascorbic acid from a beet source,
5.0 grams of thiamine hydrochloride,
0.4 grams of pyridoxal-5-phosphate monohydrate,
0.4 grams of riboflavin-5-phosphate sodium,
10.0 grams of niacinamide,
20.0 grams of dexpanthenol,
10.0 grams of inositol,
8.0 grams of magnesium chloride,
12.8 grains of zinc sulfate,
1.572 grams of cupric sulfate,
0.612 grams of manganese sulfate,
0.02052 grams of chromic chloride,
0.0392 grams of sodium selenite, and
saline solution to bring the total volume to 1000 milliliters.

2. A method of administering an anti-craving medication to the body of an individual suffering from substance abuse, the method comprising:

administering a bolus of an anti-craving medication via direct injection; and administering an anti-craving medication in an intravenous drip, wherein the anti-craving medication comprises:
7.50 grams of D-phenylalanine,
7.50 grams of L-phenylalanine,
0.05 grams of L-tyrosine,
2.4 grams of L-tryptophan,
15.0 grams of L-glutathione,
2.0 grams of folic acid,
0.4 grams of methylcobalamin,
500 grams of ascorbic acid from a beet source,
5.0 grams of thiamine hydrochloride,
0.4 grams of pyridoxal-5-phosphate monohydrate,
0.4 grams of riboflavin-5-phosphate sodium,
10.0 grams of niacinamide,
20.0 grams of dexpanthenol,
10.0 grams of inositol,
8.0 grains of magnesium chloride,
12.8 grams of zinc sulfate,
1.572 grams of cupric sulfate,
0.612 grams of manganese sulfate,
0.02052 grams of chromic chloride,
0.0392 grams of sodium selenite, and
saline solution to bring the total volume to 1000 milliliters.

* * * * *